United States Patent [19]

Siegel

[11] Patent Number: 5,025,786
[45] Date of Patent: Jun. 25, 1991

[54] INTRACARDIAC CATHETER AND METHOD FOR DETECTING AND DIAGNOSING MYOCARDIAL ISCHEMIA

[76] Inventor: Sharon B. Siegel, 555 Laurel Ave., San Mateo, Calif. 94401

[21] Appl. No.: 222,217

[22] Filed: Jul. 21, 1988

[51] Int. Cl.$^5$ .......................................... A61B 5/0402
[52] U.S. Cl. .................................... 128/642; 128/673
[58] Field of Search ...................... 128/642, 673–675, 128/670, 700

[56] References Cited

U.S. PATENT DOCUMENTS

| | | | |
|---|---|---|---|
| 3,995,623 | 12/1976 | Blake et al. | 128/642 |
| 4,585,013 | 4/1986 | Harris | 128/785 |
| 4,681,117 | 7/1987 | Brodman et al. | 128/642 |

FOREIGN PATENT DOCUMENTS 1192263 8/1985 Canada ................................ 128/642

OTHER PUBLICATIONS

Chatterjee et al, "Multipurpose Flotation Electrode Catheter", Am. J. Card., vol. 33, p. 130, Jan. 1974.
Ganz et al, "Newer Applications . . . Disease", Med. Inst., vol. 6, #2, Mar.-Apr. 1972, p. 167.
Siegel, et al.; "Intracardiac Electrode Detection of Early or Subendocardial Ischemia"; Nov.-Dec. 1982, pp. 892-902.
Siegel, et al.; "Detection of Ischemia with an Intracavitary Electrode", Pace, vol. 5, Mar.-Apr. 1982, p. 307 (Abstract).
Siegel, et al.; "Intracardiac Electrode Detection of Early or Subendocardial Ischemia"; Circulation vol. 66, Part 2, p. 367, Oct. 1982 (Abstract).
Siegel, et al.; "Intracardiac Electrode Detection of Early Ischemia Prior to the Onset of Ventricular Fibrillation"; Pace, vol. 6, p. A-136 (Abstract).
Brodman and Siegel, et al.; "Detection of Ischemia Presaging Ventricular Arrhythmias in Canines"; Chest, vol. 86, p. 324, 1984 (Abstract).

Primary Examiner—Lee S. Cohen
Attorney, Agent, or Firm—Lawrence N. Ginsberg

[57] ABSTRACT

An intracardiac catheter and method for detecting and diagnosing myocardial ischemia. The intracardiac catheter comprises a flexible, elongated body which is insertable into the heart of the subject. The distal portion of the catheter is insertable into the ventricle of the heart while an intermediate portion is insertable into an adjacent body chamber, likely the atrium. The catheter includes electrical sensing means having at least one sensing electrode at the distal end portion for measuring the electrical activity in the ventricle and means for preventing the sensing electrode from coming into direct contact with the endocardium. Pressure sensing means is provided on, at least the intermediate portion. The catheter has the capability of providing simultaneous indications of electrical activity within the ventricle and pressure within the adjacent body chamber, thus permitting correlation between indications of pressure and electrical activity.

21 Claims, 2 Drawing Sheets

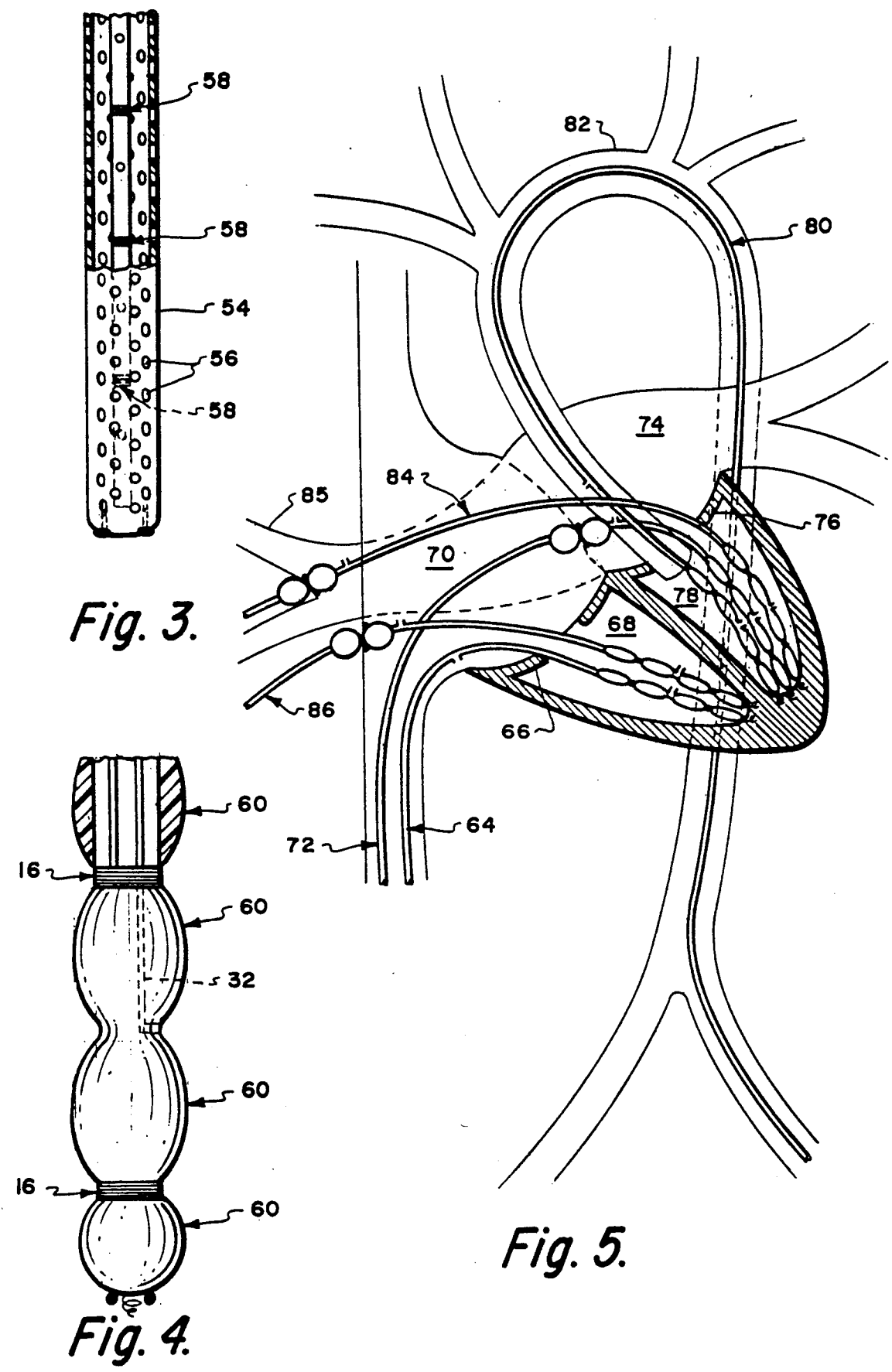

INTRACARDIAC CATHETER AND METHOD FOR DETECTING AND DIAGNOSING MYOCARDIAL ISCHEMIA

BACKGROUND OF THE INVENTION

1. Field of the Invention

This invention generally relates to intracardiac instruments and methods, and more particularly to an intracardiac catheter and a method with the capability for electrical sensing, pressure sensing and cardiac pacing that is especially well suited for detecting, diagnosing, and treating myocardial ischemia.

2. Description of Related Art

Present applicant has previously demonstrated the efficacy of utilizing a specially designed intracardiac catheter for detecting ischemia induced experimentally by partial coronary artery stenosis in dogs. (See the paper entitled "Intracardiac Electrode Detection of Early or Subendocardial Ischemia" by S. Siegel, et. al, Pace, Vol. 5, December 1982, pages 892–902. Also, the abstracts entitled "Detection of Ischemia with an Intracavitary Electrode" by S. Siegel, et. al, Pace, Vol. 5, March–April 1982, page 307; "Intracardiac Electrode Detection of Early or Subendocardial Ischemia" by S. Siegel et. al, Circulation Vol. 66 Part II, page 367; Onset of Ventricular Fibrillation" by S. Siegel et. al, Pace, Vol. 6, page A-136; and "Detection of Ischemia Presaging Ventricular Arrhythmias in Canines" by R. Brodman, S. Siegel et. al, Chest, Vol. 86, page 324.) The catheter disclosed in the above references included an elongated body having a lumen form therein. Electrical conducting means was contained within the lumen extending from a monitor at the proximal end to an electrical activity sensing electrode at the distal end.

The distal end of the catheter was placed in the ventricle of the heart. Analysis of resulting electrocardiographs demonstrated a correlation between the stenoses produced and the sensed electrogram.

Although potentially useful for detecting ischemia, the intracardiac catheter utilized in those references may have detected a variety of superimposed variables. The proximity of the sensing electrode to the ischemic area may have been variable and was not evaluated. Cardiac function may change drastically within seconds based upon any number of variable factors which are interrelated such as changes in volume status, peripheral vascular resistance, heart rate, rhythm and cardiac output. Cardiac output may significantly affect myocardial function and secondarily result in changes in myocardial perfusion or ischemia.

Proper diagnosis of ischemia as a primary event (e.g. spasm, graft closure, coronary thrombosis causing ischemia) or secondary event (e.g. due to hypovolumia; hypertension; tachycardia; bradycardia; pulmonary edema; loss of atrial kick; drop in cardiac output; etc.) is critical to accurate diagnosis and formulation of an appropriate plan of treatment. Thus, the previously disclosed catheter, although useful in detecting myocardial ischemia, lacked the capacity to diagnose and treat the problem.

OBJECTS AND SUMMARY OF THE INVENTION

It is a primary object of the present invention, therefore, to effectively diagnose and treat myocardial ischemia.

It is another object to permit simultaneous, reliable, and instantaneous detection of multiple crucial variables, critical in producing or resulting from myocardial ischemia, including intracavitary pressure, rhythm, rate intracardiac electrogram—thus permitting appropriate evaluation, diagnosis and treatment and improve myocardial salvage.

It is another object to provide a means for pacing the atrium and/or ventricle, thus optimizing oxygen supply and hemodynamics of the heart with continuous feedback.

Other objects, advantages and novel features of the present invention will become apparent from the following detailed description of the invention when considered in conjunction with the accompanying drawing.

The invention is an intracardiac catheter and method for diagnosing and treating myocardial ischemia. In its broadest aspects, the intracardiac catheter comprises a flexible, elongated body which is insertable into the heart of the subject. The distal portion of the catheter is insertable into the ventricle of the heart while an intermediate portion is located in an adjacent body chamber, preferably the atrium. The catheter includes electrical sensing means having at least one sensing electrode at the distal end portion for measuring the electrical activity in the ventricle and means for preventing the sensing electrode from coming into direct contact with the endocardium. Pressure sensing means is provided on the intermediate portion. The catheter has the capability of providing simultaneous indications of electrical activity within the ventricle and pressure within the adjacent body chamber, thus permitting correlation between indications of pressure and electrical activity. This correlation is necessary in order to help determine whether the ischemia is a primary event or the result of some other condition, such a determination being critical for formulating an appropriate plan of treatment.

Preferably, the catheter includes balloons for preventing the sensing electrode or electrodes from coming into contact with the endocardium. However, a variety of other means may be utilized such as beads. It is also preferable to have pacing electrodes attached to the end balloon for pacing the heart. With the utilization of a single unit providing the capability of simultaneous input and analysis of various parameters (i.e. electrical activity at different locations, pressures at different locations) extremely effective feedback is provided for optimal pacing, volume, drug administration or other treatment. In this spirit it is contemplated that various combinations of sensing electrodes, pressure sensors, and balloons may be utilized, as described below.

BRIEF DESCRIPTION OF THE DRAWINGS

FIG. 3 is an illustration of a portion of an intracardiac catheter in accordance with an alternate embodiment of the invention in which perforated insulating material encircles the electrical activity sensing means.

FIG. 4 illustrates an alternate embodiment in which beads are utilized.

FIG. 5 is a simplified, cross-sectional view of a heart, with intracardiac catheters built in accordance with the present invention placed in the left and right ventricles by the transvenous, transeptal, transarterial and intraoperative approaches.

DETAILED DESCRIPTION OF THE PREFERRED EMBODIMENTS

Figures 1, 2:
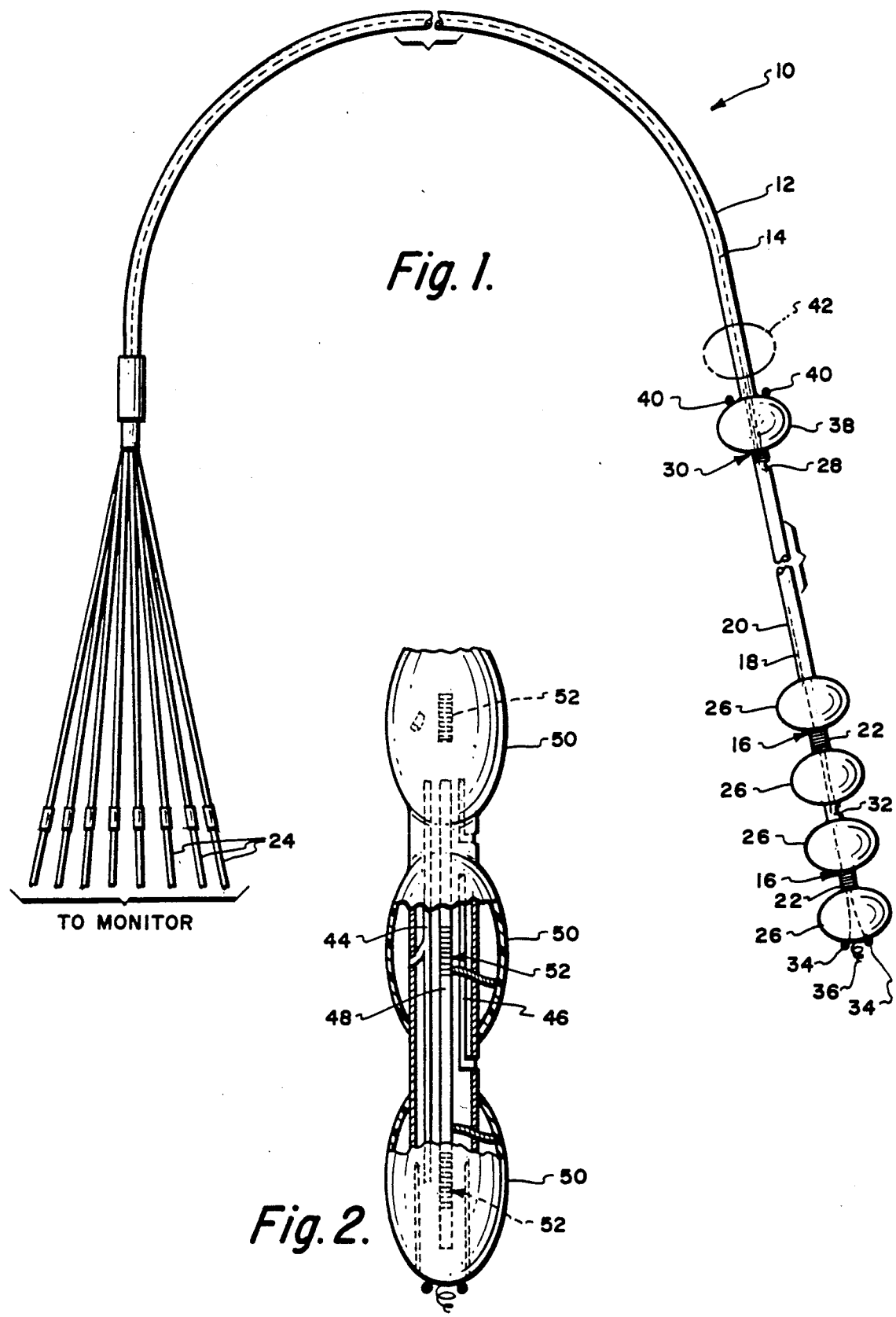
FIG. 1 is a perspective view of a preferred embodiment of the intracardiac catheter of the present invention.
FIG. 2 is a front view, partially in cross-section, of an alternate embodiment of the present invention in which the balloons surround the electrical sensing means.

Referring to the drawings and the characters of reference marked thereon the intracardiac catheter of the present invention is designated generally as 10 in FIG. 1. The catheter 10 includes a flexible, elongated body having an outer wall 12 defining a lumen 14 which extends the length of the body. The catheter 10 contains electrical activity sensing means, designated generally as 16 for measuring the electrical activity in a ventricle of the heart. Means 16 includes at least one distally extending electrical conductor 18 extending within the lumen 14 from the proximal end portion to a distal end portion. An electrically insulating sheath 20 covers a substantial portion of the electrical conductor 18. Sensing electrode means 22 are connected to the distal end of the conductor 18 for detecting electric currents from the ventricle. Plugs 24 are connected to the proximal end of the conductor 18 for connection to an external monitoring source (not shown).

The intracardiac catheter 10 includes means 26, secured to the elongated body, for preventing the sensing electrode means 22 from coming into direct contact with the endocardium of the heart. The intracardiac catheter 10 further includes pressure sensing means 28 for sensing pressure at an intermediate portion of the intracardiac catheter. Means 28 comprising a pressure port functions to measure pressure in a body chamber adjacent the ventricle, most likely the atrium.

Another electrical activity sensing means, designated generally as 30 may be utilized at the intermediate portion and is particularly useful for rhythm and rate determinations.

In the preferred embodiment illustrated in FIG. 1, the electrical activity sensing means 16 includes several distally extending, parallel pathed electrical conductors 18 terminating with axially spaced-apart sensing electrodes 22. Preventing contact of the sensing electrodes 22 with the endocardium of the heart is required in order to prevent obscuration of the sensed electrical currents by a current of injury or interference patterns. The means 26 for preventing contact may, as illustrated in FIG. 1, include inflatable balloons. Balloons 26 may be inflated or deflated by injection or aspiration by conduit and valve means more fully described below.

Ventricular pressure sensing may be accomplished by at least one pressure port 32. The pressure port 32 is located in close proximity to its adjacent balloons. Thus, the balloons, as well as preventing contact of the electrical sensing electrode means 16 with the endocardium, also prevent contact of the pressure port 32 with the endocardium. This prevents obscuration of the sensed pressure by interference patterns and assures an accurate pressure tracing. There may be a plurality of pressure ports, for example, also between the most distally positioned balloon and the adjacent balloon.

The most distally positioned balloon potentially extends beyond the length of the elongated body, as illustrated in FIG. 1. It may have pacing electrodes 34 attached, as illustrated. Pacing electrodes 34 permit cardiac pacing. Their position on the balloon assures sufficient contact so as to provide an efficient pacing. A commercially available fixation device 36, such as a screw-in device locatable at the catheter tip may also be utilized when deemed necessary.

Another balloon, designated 38, is located on the intermediate portion of the catheter 10. During use, when the catheter is passed through the atrium, the balloon 38 abuts the atrial wall and prevents the catheter from potentially sliding or being pulled out inadvertently. In addition, it prevents the pressure sensing port 28 from coming into contact with the atrial wall, thus preventing distortion of the sensed pressure wave by interference. The balloon is deflated in order to permit removal of the catheter. Pacing electrodes 40 are shown positioned on the balloon 38 so as to assure continuous contact of the electrodes 40 with the atrial wall and thus provide reliable atrial pacing.

Another balloon, designated 42, illustrated in phantom, is locatable on the other side of the atrial wall opposite balloon 38 as a further means for securely positioning the catheter 10. Movement of the catheter within the heart may result in misleading changes of data input into the monitor. Together with the fixation device 36, utilization of balloons 38, 42 maintains a relatively fixed relationship between the catheter 10 and the endocardium.

Referring now to FIG. 2, a portion of a catheter is illustrated in which a plurality of axially-spaced balloons 50 are utilized and sufficiently spaced to form axially-spaced enclosed and unenclosed sections on the distal end portion of the elongated body. The electrical activity sensing means 52 are enclosed by the balloons 50. (Thus this embodiment is distinguished from that described with reference to FIG. 1 in which the electrical activity sensing means lies outside of the balloon enclosed region.) A conduit 44 is included which extends through the lumen 46 adjacent the electrical conductor 48 and in communication with inflatable balloons 50. The conduit 44 may provide a physiologic electrolyte solution such as saline or blood from a reservoir or source located outside a patient for the balloons 50 to inflate the balloons when the electrical sensing means 52 is within the ventricle and to conduct the solution therefrom to collapse the balloons 50 prior to removal of the catheter 10. With a conductive solution in the embodiment of FIG. 2, the electrical sensing means 52 detects electric currents emanating from the blood surrounding conductive balloons 50 via the conductive solution in communication with the interior of the balloons 50.

As will be appreciated, other arrangements may be employed to prevent the electrical activity sensing means and pressure sensing means from coming into direct contact with the heart. For example, as shown in FIG. 3, insulating material 54 having one or a plurality of openings 56, encircles electrical sensing means 58. Or, other radially outward extending means may be utilized. For example, flaps may be utilized (not illustrated) which extend axially against the outer wall of the elongated body in constricted position during insertion and removal of the catheter. Upon positioning within the body chamber, the flaps would extend radially outward.

FIG. 4 illustrates yet another alternative means for preventing contact of the electrical sensing means with the endocardium of the heart. In this embodiment axially spaced beads 60 prevent such a contact.

The catheter of the present invention may be inserted during a surgical procedure or without such a procedure, transvenously, transeptally or transarterially. Referring now to FIG. 5, a simplified illustration of the heart, during a laboratory procedure, the catheter may be positioned from a venipuncture made in an arm vein, the subclavian vein, or femoral vein into the inferior or superior vena cava, and into the right atrium 70. For right-sided catheterization, the catheter, in this case designated generally as 64 can be passed through the tricuspid valve 66 and the distal portion positioned in the right ventricle 68, the intermediate portion being located in the right atrium 70. For left-sided transvenous catheterization, the catheter, in this case designated generally as 72 can be passed transeptally from the right atrium 70 to the left atrium 74 and then across the mitral valve 76 into the left ventricle 78. The intermediate portion of the catheter 72 would be located in the left atrium 74. Alternatively a catheter, designated generally as 80, may be inserted, in the laboratory, via a brachial or femoral artery through the aorta 82 into the left ventricle 78. In this scenario, the intermediate portion transmits data from the aorta 82 simultaneous with transmission of data from the left ventricle 78.

During open heart surgery the catheter would be particularly useful. Current available means of monitoring electrical activity of the heart during these long procedures is generally inadequate. The catheter, in this case designated generally as 84, can be inserted through a purse string on the superior pulmonary vein 85, through the left atrium 74, mitral valve 76, and positioned in the left ventricle 78. In less frequent situations, a catheter designated 86 can be inserted through a purse string on the wall of the right atrium 70 through the right atrium 70, the tricuspid valve 66 and into the right ventricle 68. In both cases the catheter traverses the mediastinum and passes out the chest wall through a pull-away introducer needle. The catheter could be removed a few days post operatively when no longer needed by simply deflating the balloons and pulling it out from where it exits from the chest wall. In the scenarios in which the catheter is inserted into the left ventricle by the transeptal or intraoperative approach, the intermediate portion is located in the left atrium (i.e. adjacent body cavity). When the catheter is positioned in the left ventricle by a transarterial approach (only used in particular circumstances) the intermediate portion is located in the aorta. In this instance no balloon would be utilized on the intermediate portion.

When the catheter is utilized, multiple parameters are being simultaneously monitored. If the measured intracardiac electrogram (i.e. data from electrical activity sensing means) exhibits a change pattern characteristic of ischemia, then the physician may immediately evaluate other simultaneously recorded parameters including vital signs, rate, rhythm, and left atrial pressure. If the patient is found to be bradycardic (slow heart rate), tachycardic (fast heart rate), in a junctional or ventricular rhythm then drugs can be administered or pacing instituted to correct the problem. If the patient is found to be hypotensive or hypertensive then fluid or drug manipulations could be instituted. If the patient is found to be hypovolumic (low atrial pressure) then transfusion or fluid administration would be initiated. If the patient is in pulmonary edema (high atrial pressure) then diuresis, vasodilation or isotopic support could be instituted.

The effect and degree of any of these interventions on the ischemic change can be assessed on a moment to moment basis and thus be curtailed or altered accordingly. If treatment of one of the above problems corrects the ischemia then nothing more need be done. If correction of all other parameters leaves persistent ischemia present then diagnosis of primary ischemia may be made and treatment of primary ischemia may be instituted.

Treatment of primary ischemia may include use of nitrates, or calcium blockers for spasm; anticoagulation for thrombosis; or angioplasty or surgery for occlusion. The efficacy of any intervention could be evaluated and titrated by continuous monitoring of all of the parameters as well as the intracardiac electrogram.

The importance of the simultaneous evaluation of all parameters is illustrated by the scenario below:

If ischemic change is detected on the electrogram and the other parameters not evaluated then the patient might be given a calcium blocker or nitrate. If hypovolemia or junctional rhythm are present then these could be made worse resulting in worsening of the ischemia with potential irreversible and disastrous results.

Therefore, as the above example illustrates, it is not only the detection of ischemia that is important but also the diagnosis of whether the ischemia is primary or secondary which is critical to the proper management thereof.

Obviously many modifications and variations of the present invention are possible in light of the above teachings. It is therefore to be understood that, within the scope of the appended claims, the invention may be practiced otherwise than as specifically described.

For example, although FIGS. 1 and 2 show a plurality of balloons which form a plurality of balloon enclosed and unenclosed sections along the distal end portion it is clear that a single balloon or other means for preventing contact may be utilized in either embodiment. Furthermore, although a plurality of sensing electrodes are illustrated along the distal end portion a single sensing electrode may be utilized. The particular combination of balloons, pressure sensors, sensing electrodes and pacing electrodes should be arranged according to the intended use.

What is claimed and desired to be secured by Letters Patent of the United States is:

1. An intracardiac catheter for sensing electrical activity and pressure within the heart of a living subject and for transmitting indications of this electrical activity and pressure to an external monitoring source, comprising:

a) a flexible elongated body having an outer wall defining a lumen formed therein extending the length of said elongated body, said body having a proximal end portion and a distal end portion;

b) electrical activity sensing means for measuring the electrical activity in a ventricle of the heart, including, at least one distally extending electric conductor having a proximal end and a distal end, said electric conductor extending within said lumen from said proximal end portion to said distal end portion, an electrically insulating sheath covering a substantial portion of said electric conductor, sensing electrode means connected to the distal end of the conductor, said sensing electrode means being capable of detecting electric currents from the ventricle, and means connected to the proximal end of the conductor to connect the electric conductor to said external monitoring source;

c) means secured to the elongated body for preventing the sensing electrode means from coming into direct contact with the endocardium of the heart plus preventing obscuration of the sensed electrical currents by interference patterns; and d) pressure sensing means for sensing pressure in a body chamber adjacent said ventricle, said pressure sensing means extending within said lumen from an intermediate portion located between the distal portion and the proximal portion to said proximal portion, said pressure sensing means being connectable at a proximal end to said external monitoring source, wherein during utilization of the catheter said intermediate portion is positioned within said body chamber adjacent said ventricle and said distal portion is positioned in a ventricle of the heart, the catheter therefore having the capability of providing simultaneous indications of electrical activity within the ventricle and pressure within the adjacent body chamber, thus permitting correlation between indications of pressure and electrical activity.

2. The intracardiac catheter of claim 1 further including, ventricular pressure sensing means extending within said lumen from said distal portion to said proximal portion, said ventricular pressure sensing means having a distal end in sufficient proximity to said means for preventing contact so as to prevent contact of said distal end with the endocardium of the heart, said ventricular pressure sensing means being connectable at a proximal end thereof to said external monitoring source for providing indications of pressure within said ventricle during operation thereof.

3. The intracardiac catheter of claim 2 wherein:

said ventricular pressure sensing means includes a plurality of axially spaced pressure sensors.

4. The intracardiac catheter of claim 1 wherein said adjacent chamber is an atrium, the catheter further including means secured to said elongated body at said intermediate portion for securely positioning the catheter and for preventing said pressure sensing means from coming into direct contact with the atrium, thus preventing distortion of the sensed pressure wave by interference.

5. The intracardiac catheter of claim 4 further including, atrial pacing means extending within said lumen from said proximal end portion and terminating with an atrial pacing electrode located on said means secured to said elongated body at said intermediate portion for securely positioning the catheter, said means for securing positioning including radially extending means which maintains contact with the atrial wall, said atrial pacing electrode being attached to and positioned with respect to said radially extending means so that the atrial pacing electrode is kept in contact with the atrial muscle so as to provide efficient pacing.

6. The intracardiac catheter of claim 4 wherein said means for securely positioning the catheter at said intermediate portion includes balloon means for such a secure positioning.

7. The intracardiac catheter of claim 4 wherein said means for securing said catheter at said intermediate portion includes first radially extending means locatable at a position proximal to the atrial wall and second radially extending means locatable distal to the atrial wall.

8. The intracardiac catheter of claim 1 further including, second electrical activity sensing means for measuring the electrical activity in said adjacent body chamber, having, at least one intermediate electric conductor extending within said lumen from a first end at said proximal end portion to a second end at said intermediate portion;

an intermediate electrically insulating sheath covering a substantial portion of said intermediate electric conductor;

intermediate sensing electrode means connected to the second end of the intermediate electric conductor, said intermediate electrode sensing means being capable of detecting electric currents in the adjacent body chamber;

means connected to a proximal end of the intermediate electric conductor to connect the intermediate electric conductor to said external monitoring source; and means secured to the intermediate portion of said elongated body for securely positioning the catheter and preventing the intermediate sensing electrode means from coming into direct contact with the endocardium of the heart.

9. The intracardiac catheter of claim 1, wherein, said electrical activity sensing means for measuring the electrical activity in the ventricle of the heart includes, a plurality of distally extending electric conductors having parallel paths from said proximal end portion to said distal end portion, each electric conductor having a respective insulating sheath and a sensing electrode connected to its distal end, each sensing electrode being capable of detecting electric currents from the ventricle, said sensing electrodes being axially spaced apart within said distal end portion, said means for preventing the sensing electrode means from coming into direct contact with the endocardium, including means secured to said elongated body for preventing said sensing electrodes from coming into direct contact with the endocardium of the heart for preventing obscuration of the sensed electrical currents by interference patterns.

10. The intracardiac catheter of claim 1 further including, ventricular pacing means extending within said lumen from said proximal end portion and terminating at said distal end portion for providing electrical impulses to said endocardium in response to said indications of electrical activity and pressure.

11. The intracardiac catheter of claim 1 wherein the means for preventing the sensing means from contacting the endocardium includes electrically conductive balloon means for enclosing the sensing electrode means.

12. The intracardiac catheter of claim 11 wherein said balloon means includes a single balloon.

13. The intracardiac catheter of claim 11 wherein said balloon means includes a plurality of axially-spaced balloons.

14. The intracardiac catheter of claim 1, wherein:

said electrical activity sensing means for measuring the electrical activity in the ventricle of the heart includes, a plurality of distally extending electric conductors having parallel paths from said proximal end portion to said distal end portion, each electric conductor having a respective insulating sheath and a sensing electrode connected to its distal end, each sensing electrode being capable of detecting electric currents from the ventricle, said sensing electrodes being axially spaced apart within said distal end portion, and said means for preventing said sensing electrode means from coming into direct contact includes a plurality of axially-spaced balloons being sufficiently spaced so as to form axially alternating balloon enclosed and unenclosed sections on the distal end portion of said elongated body, each said sensing electrode being located at one of said unenclosed sections, the balloon or balloons located adjacent to or being in sufficiently close proximity thereto so as to prevent contact of the sensing electrode with the endocardium of the heart.

15. The intracardiac catheter of claim 14 including a single ventricular pressure sensor.

16. The intracardiac catheter of claim 14 wherein said ventricular pressure sensing means includes a plurality of pressure ports, each being located in an unenclosed section in sufficiently close proximity to a balloon so as to prevent its contact with the endocardium of the heart.

17. The intracardiac catheter of claim 1 wherein said means for preventing the sensing electrode means from coming into direct contact with the endocardium includes radially extending means for urging said distal end portion of said elongated body away from the endocardium.

18. The intracardiac catheter of claim 17 wherein said radially extending means includes balloon means for such a radial extension.

19. The intracardiac catheter of claim 18 wherein:

said electrical activity sensing means for measuring the electrical activity in the ventricle of the heart includes, a plurality of distally extending electric conductors having parallel paths from said proximal end portion to said distal end portion, each electric conductor having a respective insulating sheath and a sensing electrode connected to its distal end, each sensing electrode being capable of detecting electric currents from the ventricle, said sensing electrodes being axially spaced apart within said distal end portion, and said means for preventing said sensing electrode means from coming into direct contact includes a plurality of axially-spaced balloons being sufficiently spaced so as to form axially alternating balloon enclosed and unenclosed sections on the distal end portion of said elongated body, each said sensing electrode being located at one of said unenclosed sections, the balloon or balloons located adjacent to or being in sufficiently close proximity thereto so as to prevent contact of the sensing electrode with the endocardium of the heart.

20. The intracardiac catheter of claim 17 wherein said radially extending means includes bead means for such a radial extension.

21. A method for detecting and diagnosing myocardial ischemia in a living subject, comprising:

a) inserting a catheter into the heart of the subject intraoperatively or in the laboratory transvenously, transeptally or transarterially, said catheter having sensing electrode means at a distal end portion which is insertable into a ventricle of the heart and pressure sensing means at an intermediate portion of the catheter which is insertable into a body chamber adjacent said ventricle;

b) preventing said sensing electrode means from coming into direct contact with the endocardium of the heart thus preventing obscuration of the sensed electrical currents by interference patterns;

c) sensing the electrical activity in the ventricle, with the sensing electrode means and pressure within the adjacent body chamber with the pressure sensing means;

d) correlating the sensed electrical activity and pressure within the adjacent body chamber for evaluating the status of the heart and thereby permitting a diagnosis and treatment of myocardial ischemia.

* * * * *